US00PP28037P3

(12) United States Plant Patent
Danziger

(10) Patent No.: US PP28,037 P3
(45) Date of Patent: May 16, 2017

(54) *DIASCIA* PLANT NAMED 'DDIASC990'

(50) Latin Name: *Diascia barberae*
Varietal Denomination: DDIASC990

(71) Applicant: Gavriel Danziger, Moshav Mishmar Hashiva (IL)

(72) Inventor: Gavriel Danziger, Moshav Mishmar Hashiva (IL)

(73) Assignee: Danziger "DAN" Flower Farm, Moshav Mishmar Hashiva (IL)

( * ) Notice: Subject to any disclaimer, the term of this patent is extended or adjusted under 35 U.S.C. 154(b) by 55 days.

(21) Appl. No.: 14/756,435

(22) Filed: Sep. 4, 2015

(65) Prior Publication Data

US 2017/0071120 P1 Mar. 9, 2017

(51) Int. Cl.
*A01H 5/02* (2006.01)

(52) U.S. Cl.
USPC ..... Plt./425

(58) Field of Classification Search
USPC ..... Plt./425
See application file for complete search history.

*Primary Examiner* — Keith Robinson
(74) *Attorney, Agent, or Firm* — C. A. Whealy

(57) ABSTRACT

A new and distinct cultivar of *Diascia* plant named 'DDIASC990', characterized by its compact, semi-upright and uniformly mounding plant habit; freely branching habit; strong flowering stems; numerous large pure white-colored flowers with dark yellow-colored throats; and good garden performance and tolerant to high temperatures.

2 Drawing Sheets

Botanical designation: *Diascia barberae*.
Cultivar denomination: 'DDIASC990'.

BACKGROUND OF THE INVENTION

The present invention relates to a new and distinct cultivar of *Diascia* plant, botanically known as *Diascia barberae* and hereinafter referred to by the name 'DDIASC990'.

The new *Diascia* plant is a product of a planned breeding program conducted by the Inventor in Moshav Mishmar Hashiva, Israel. The objective of the breeding program is to create new compact and freely flowering *Diascia* plants that tolerate high temperatures.

The new *Diascia* plant originated from an open-pollination in April, 2010 in Moshav Mishmar Hashiva, Israel of a proprietary selection of *Diascia barberae* identified as code number DI-10-1730, not patented, as the female, or seed, parent and with an unknown selection of *Diascia barberae* as the male, or pollen, parent. The new *Diascia* plant was discovered and selected by the Inventor as a single flowering plant from within the progeny of the stated open-pollination in a controlled greenhouse environment in Moshav Mishmar Hashiva, Israel in July, 2011.

Asexual reproduction of the new *Diascia* plant by vegetative terminal cuttings in a controlled greenhouse environment in Moshav Mishmar Hashiva, Israel since July, 2011 has shown that the unique features of this new *Diascia* plant are stable and reproduced true to type in successive generations.

SUMMARY OF THE INVENTION

Plants of the new *Diascia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DDIASC990'. These characteristics in combination distinguish 'DDIASC990' as a new and distinct *Diascia* plant:

1. Compact, semi-upright and uniformly mounding plant habit.
2. Freely branching habit.
3. Strong flowering stems.
4. Numerous large pure white-colored flowers with dark yellow-colored throats.
5. Good garden performance and tolerant to high temperatures.

Plants of the new *Diascia* can be compared to plants of the female parent selection. Plants of the new *Diascia* differ primarily from plants of the female parent selection in the following characteristics:

1. Plants of the new *Diascia* are more compact and uniformly mounding than plants of the female parent selection.
2. Plants of the new *Diascia* are tolerant to high temperatures whereas plants of the female parent selection are not tolerant to high temperatures.

Plants of the new *Diascia* can be compared to plants of the *Diascia barberae* 'DGENT30', not patented. In side-by-side comparisons conducted in Moshav Mishmar Hashiva, Israel, plants of the new *Diascia* differed primarily from plants of 'DGENT30' in the following characteristics:

1. Plants of the new *Diascia* were more compact than plants of 'DGENT30'.
2. Plants of the new *Diascia* had shorter leaves than plants of 'DGENT30'.
3. Plants of the new *Diascia* differed in flower color as plants of 'DGENT30' had lighter yellow-colored flower throats and under low temperatures, petals of plants of 'DGENT30' developed a pink-colored blush.

BRIEF DESCRIPTION OF THE PHOTOGRAPHS

The accompanying colored photographs illustrate the overall appearance of the new *Diascia* plant showing the colors as true as it is reasonably possible to obtain in colored reproductions of this type. Colors in the photographs may differ slightly from the color values cited in the detailed botanical description which accurately describe the colors of the new *Diascia* plant.

The photograph on the first sheet is a side perspective view of a typical flowering plant of 'DDIASC990' grown in a container.

The photograph on the second sheet is a close-up view of a typical flower of 'DDIASC990'.

DETAILED BOTANICAL DESCRIPTION

The aforementioned photographs and following observations, measurements and values describe plants grown in 12-cm containers during the autumn in an outdoor nursery in Moshav Mishmar Hashiva, Israel and under cultural practices typical of commercial *Diascia* production. During the production of the plants, day temperatures ranged from 18° C. to 36° C., night temperatures ranged from 10° to 17° C. and light levels ranged from 7,000 to 10,000 foot-candles. Plants were pinched one time and were eight weeks old when the description was taken and nine weeks old when the photographs were taken. Supplemental flower information was collected from plants grown in 22-cm containers during the summer in an outdoor nursery in Loudon, N.H. and under cultural practices typical of commercial *Diascia* production. During the production of these plants, day temperatures averaged 27° C., night temperatures averaged 13° C. and maximum light levels were 10,000 foot-candles. These plants were pinched one time and were 18 weeks old when the supplemental flower information was taken. In the following description, color references are made to The Royal Horticultural Society Colour Chart, 2007 Edition, except where general terms of ordinary dictionary significance are used.

Botanical classification: *Diascia barberae* 'DDIASC990'.

Parentage:

*Female, or seed, parent*.—Proprietary selection of *Diascia barberae* identified as code number DI-10-1730, not patented.

*Male or pollen parent*.—Unknown selection of *Diascia barberae*, not patented.

Propagation:

*Type*.—By vegetative terminal cuttings.

*Time to initiate roots, summer*.—About six to seven days at temperatures ranging from 21° to 26° C.

*Time to initiate roots, winter*.—About eight to nine days at temperatures ranging from 21° to 26° C.

*Time to produce a rooted young plant, summer*.—About ten days at temperatures ranging from 21° to 26° C.

*Time to produce a rooted young plant, winter*.—About two weeks at temperatures ranging from 10° to 15° C.

*Root description*.—Medium in thickness, fibrous; close to 165D in color, actual color of the roots is dependent on substrate composition, water quality, fertilizer type and formulation, substrate temperature and physiological age of roots.

*Rooting habit*.—Freely branching; medium density.

Plant description:

*Plant form and growth habit*.—Compact, semi-upright and uniformly mounding plant habit; rapid growth rate; freely branching habit with about ten primary branches developing per plant.

*Plant height*.—About 17 cm.

*Plant diameter* (*area of spread*).—About 30 cm.

Lateral branch description:

*Length*.—About 17 cm.

*Diameter*.—About 2 mm.

*Internode length*.—About 2 cm to 3 cm.

*Strength*.—Moderately strong.

*Aspect*.—About 45° from vertical.

*Texture*.—Smooth, glabrous; longitudinally ridged.

*Color*.—Close to 146B.

Leaf description:

*Arrangement*.—Opposite, simple.

*Length*.—About 2 cm.

*Width*.—About 1.4 cm.

*Shape*.—Ovate.

*Apex*.—Acute.

*Base*.—Truncate.

*Margin*.—Crenate.

*Texture, upper and lower surfaces*.—Smooth, glabrous.

*Venation pattern*.—Pinnate.

*Color*.—Developing and fully expanded leaves, upper surface: Close to 137A; venation, close to 144B. Developing and fully expanded leaves, lower surface: Close to 138B; venation, close to 144A.

*Petioles*.—Length: About 3 mm. Diameter: About 2 mm. Texture, upper and lower surfaces: Smooth, glabrous. Color, upper and lower surfaces: Close to 144A.

Flower description:

*Flower arrangement and habit*.—Large single flowers arranged on terminal and axillary racemes; flowers zygomorphic with five lobes fused at the base and spurred; freely flowering habit with about five open flowers per raceme and about 600 flowers developing per plant; flowers face outwardly.

*Fragrance*.—None detected.

*Flowering response and natural flowering season*.—Early flowering habit, plants begin flowering about one month after planting; long flowering period, plants flower freely and continuously from autumn to spring in Israel.

*Flower longevity*.—Flowers last about four days on the plant; flowers not persistent.

*Inflorescence height*.—About 10 cm.

*Inflorescence diameter*.—About 5.5 cm.

*Flower diameter*.—About 2 cm by 2.5 cm.

*Flower depth*.—About 6 mm to 12 mm.

*Flower buds*.—Length: About 2 mm to 4 mm. Diameter: About 3 mm to 7 mm. Shape: Oblate. Color: Close to 146B.

*Corolla*.—Arrangement: Corolla consists of five petals modified into two small upper petals, two lateral petals and a larger lower lip petal; petals fused at the base. Upper petals lobe length: About 1 cm. Upper petals lobe width: About 1 cm. Lateral petals lobe length: About 1 cm. Lateral petals lobe width: About 5 mm. Lower petal lobe length: About 1.5 cm. Lower petal lobe width: About 1.5 cm. Upper petals lobe shape: Cordate. Lateral and lower petals lobe shape: Ovate. Upper, lateral and lower petals lobe apex: Rounded. Upper, lateral and lower petals lobe margin: Entire. Upper petals lobe texture: Smooth, glabrous. Lateral petals lobe texture: Slightly puckered, glabrous. Lower petal lobe texture: Smooth, glabrous. Upper, lateral and lower petals lobe luster: Satiny. Spur length: About 7 mm. Spur diameter: About 5 mm. Spur orientation: Reflexed and protruding from the lower surface of the lateral petals. Color, upper, lateral and lower petals: When opening and fully opened, upper surface: Close to NN155C. When opening and fully opened, lower surface: Close to N155D. Throat: Close to 12A. Spur: Close to 155C.

*Sepals*.—Appearance: Five sepals fused into a star-shaped calyx. Length: About 2 mm. Width: About 1 mm. Shape: Elliptic. Apex: Acute. Base: Truncate. Margin: Entire. Texture, upper and lower surfaces: Smooth, glabrous. Color: When opening, upper surface: Close to 137C. When opening, lower surface: Close to 137D. Fully opened, upper and lower surfaces: Close to N137A.

*Peduncles*.—Length: About 3 cm to 3.5 cm. Diameter: About 2 mm. Strength: Strong, flexible. Angle: Mostly erect to outwardly. Texture: Smooth, glabrous. Color: Close to 146A.

*Pedicels*.—Length: About 1.5 cm. Diameter: About 0.7 mm. Strength: Strong, flexible. Angle: About 45° from the peduncle axis. Texture: Smooth, glabrous. Color: Close to 146B.

*Reproductive organs*.—Androecium: Stamen number per flower: About four. Anther length: About 2 mm. Anther shape: Bi-lobed, indented. Anther color: Close to 138D. Amount of pollen: Abundant. Pollen color: Close to 13A. Gynoecium: Pistil number per flower: One. Pistil length: About 3 mm. Style length: About 1.5 mm. Style color: Close to 142B. Stigma shape: Cylindrical. Stigma color: Close to 142B. Ovary color: Close to 143C.

*Fruits*.—Length: About 5 mm. Diameter: About 2 mm. Texture: Smooth, glabrous. Color: Close to 137C.

*Seeds*.—Quantity per fruit: About 8 to 16. Length: About 1 mm. Diameter: About 1 mm. Texture: Smooth, glabrous. Color: Close to 199A.

Garden performance: Plants of the new *Diascia* have been observed to have good garden performance and to tolerate wind, rain and temperatures ranging from about 1° C. to about 36° C.

Pathogen & pest resistance: Plants of the new *Diascia* have not been observed to be resistant to pests and pathogens common to *Diascia* plants.

It is claimed:

1. A new and distinct *Diascia* plant named 'DDIASC990' as illustrated and described.

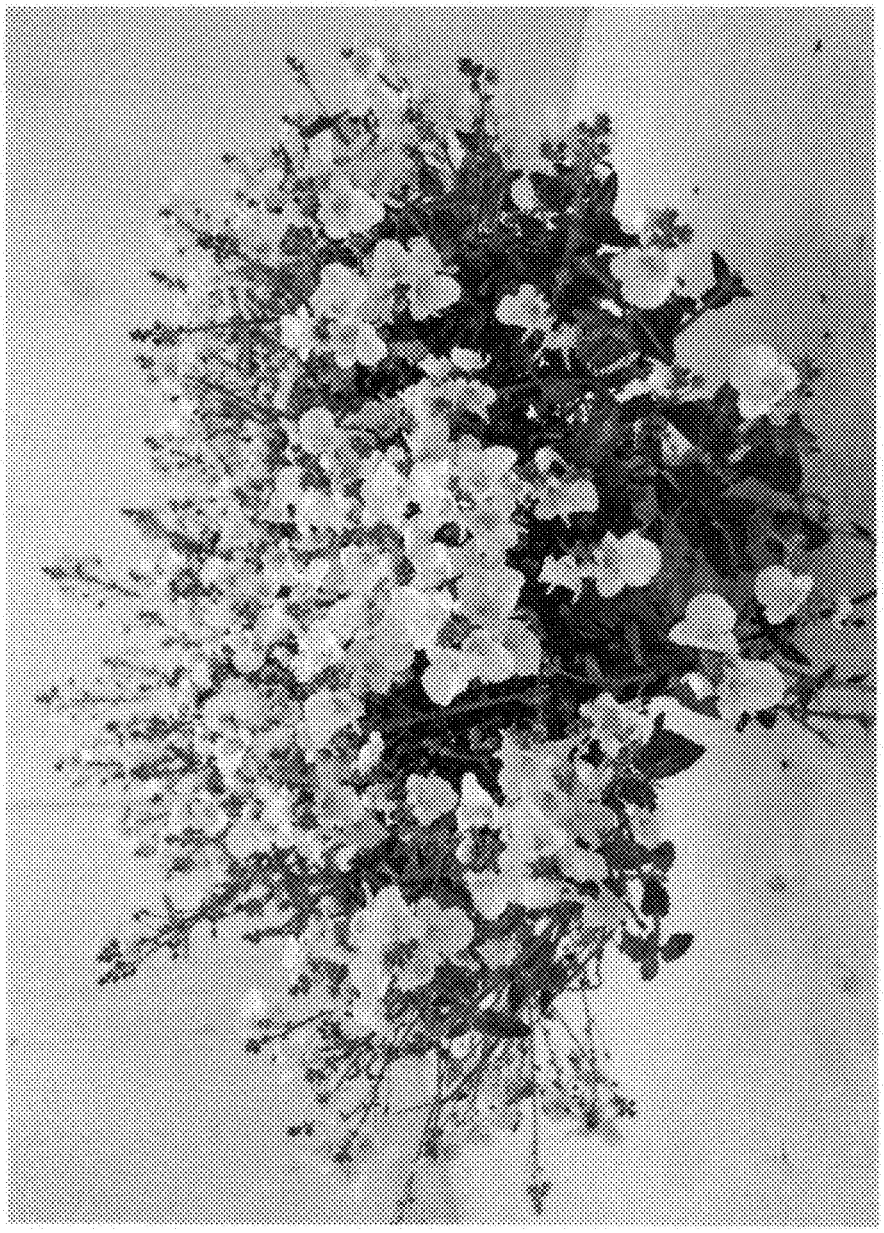

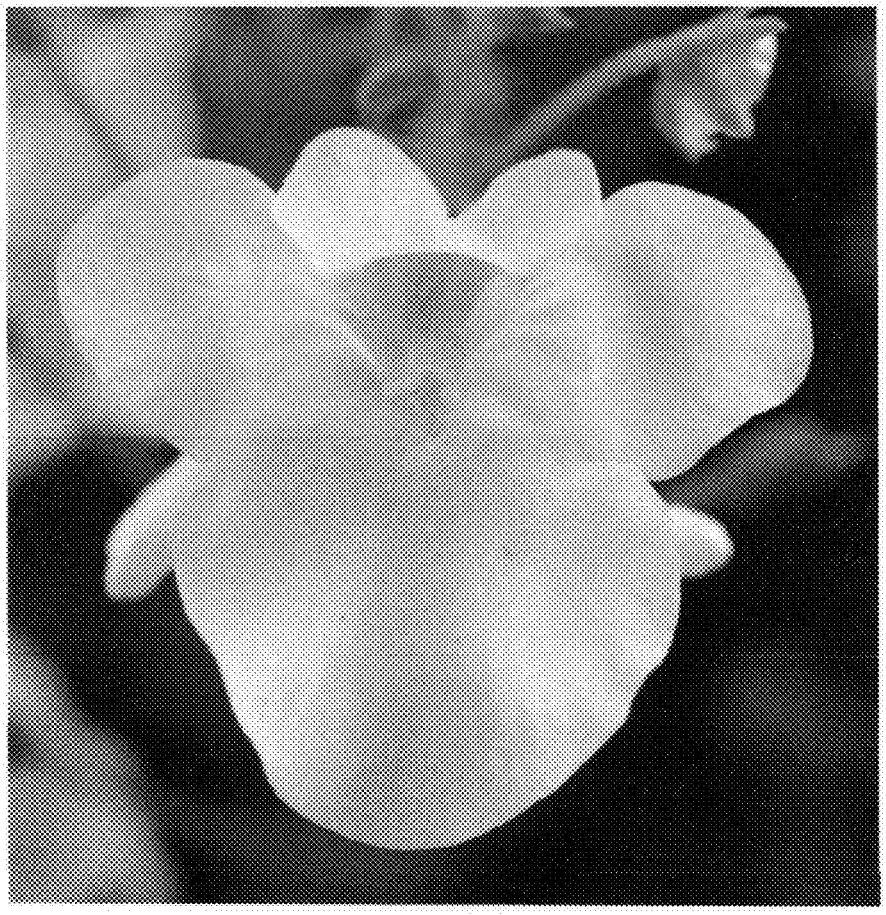

* * * * *